United States Patent [19]

Andrieux et al.

[11] Patent Number: 5,612,368
[45] Date of Patent: Mar. 18, 1997

[54] O-ARYLMETHYL-N-(THIO)ACYLHYDROXYLAMINES

[75] Inventors: Jean Andrieux, Antony; Michel Langlois, Sceaux; Pierre Renard, Versailles; Philippe Delagrange, Issy-les-Moulineaux, all of France

[73] Assignee: Adir et Compagnie, Courbevoie, France

[21] Appl. No.: 548,209

[22] Filed: Oct. 25, 1995

[30] Foreign Application Priority Data

Oct. 26, 1994 [FR] France .................. 94 12784

[51] Int. Cl.⁶ .................... A61K 31/40
[52] U.S. Cl. .................. 514/418; 514/419; 514/443; 514/469; 514/470; 514/546; 514/624; 514/629; 564/215; 564/190; 560/139; 548/472; 548/482; 549/51; 549/58; 549/466; 549/467
[58] Field of Search .................. 564/215, 190; 560/139; 548/472, 482; 514/418, 624, 629, 546, 419, 443, 469, 476; 549/51, 58, 466, 467

[56] References Cited

U.S. PATENT DOCUMENTS 4,923,896  5/1990  Trivedi .................. 514/507

OTHER PUBLICATIONS

Chem. Abstr. 113:171694, Registry No. 129951–38–8 May 8, 1990.

*Primary Examiner*—Samuel Barts
*Attorney, Agent, or Firm*—The Firm of Gordon W. Hueschen

[57] ABSTRACT

The invention relates to a compound selected from those of formula (I):

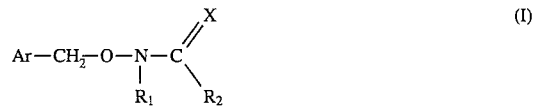

in which Ar, X, $R_1$ and $R_2$ are as defined in the description and a medicinal product containing the same in order to treat a disorder of the melatoninergic system.

10 Claims, No Drawings

O-ARYLMETHYL-N-(THIO)ACYLHY-DROXYLAMINES

The present invention relates to new O-arylmethyl-N-(thio)acylhydroxylamines, to the processes for preparing them and to the pharmaceutical compositions containing them.

The Applicant has discovered new O-arylmethyl-N-(thio)acylhydroxylamines which are potent ligands of the melatonin receptors.

In addition to their beneficial action on circadian rhythm disorders (J. Neurosurg. 1985, 63: pp 321–341) and sleep disorders (Psychopharmacology 1990; 100: pp 222–226), the compounds which act on the melatoninergic system possess valuable pharmacological properties on the central nervous system, especially anxiolytic and antipsychotic properties (Neuropharmacology of Pineal Secretions 1990, 8 (3–4): pp 264–272), and analgesic properties (Pharmacopsychiat. 1987, 20 pp 222–223), for the treatment of Parkinson's disease (J. Neurosurg 1985, 6,3: pp 321–341) and Alzheimer's disease (Brain Research 1990, 528: pp 170–174). Likewise, these compounds have exhibited activity on certain cancers (Melatonin - Clinical Perspectives, Oxford University Press, 1988: pp 164–165), on ovulation (Science 1987, 227: pp 714–720) and diabetes (Clinical endocrinology 1986, 24: pp 359–364).

More particularly, the invention relates to the compounds of formula (I):

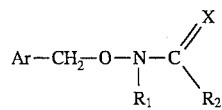

in which:
X represents an oxygen or sulfur atom,
$R_1$ represents a hydrogen atom or a radical chosen from alkyl, cycloalkyl, cycloalkylalkyl, aryl and arylalkyl,
$R_2$ represents:
 a radical $R_{21}$ which is a hydrogen or a radical chosen from:
  an unsubstituted or substituted alkyl group,
  an unsubstituted or substituted alkenyl group,
  an unsubstituted or substituted alkynyl group,
  and an unsubstituted or substituted cycloalkyl or cycloalkylalkyl group,
 or a radical $R_{22}$ chosen from:
  an alkylamino group in which the alkyl group may be unsubstituted or substituted,
  and a cycloalkylamino or cycloalkylalkylamino group in which the cycloalkyl or
  cycloalkylalkyl group may be unsubstituted or substituted,
Ar represents an unsubstituted or substituted group chosen from:
 naphthyl,
 indolyl,
 benzofuranyl,
 benzothiophenyl,
 it being possible for Ar to be partially or totally hydrogenated,
it being understood that during the description of formula (I):
 the terms "alkyl" and "alkoxy" designate linear or branched groups containing from 1 to 6 carbon atoms,
 the terms "alkenyl" and "alkynyl" designate unsaturated linear or branched groups containing from 2 to 6 carbon atoms,
 the term "cycloalkyl" designates a group of 3 to 8 carbon atoms,
 the term "substituted" associated with the alkyl, cycloalkyl, alkenyl, alkynyl and cycloalkylalkyl groups means that the substitution may be made by one or more radicals chosen from halogen, alkyl and alkoxy,
 the term "substituted" associated with the Ar group means that Ar is substituted with one or more radicals R, which are identical or different, chosen from halogen, hydroxyl, Ra, —$CH_2$—Ra, —O—Ra, —CO—Ra and —O—CO—Ra (with Ra chosen from alkyl, substituted alkyl, alkenyl, alkynyl, cycloalkyl, substituted cycloalkyl, cycloalkylalkyl, substituted cycloalkylalkyl, aryl, substituted aryl, arylalkyl and substituted arylalkyl),
 and the term "substituted" associated with the expressions "aryl" and "arylalkyl" means that the substitution consists of one or more radicals chosen from halogen, alkyl, alkoxy, hydroxy and alkyl substituted with one or more halogens;
and their enantiomers or diastereoisomers.

In a particular manner, the invention relates to the compounds of formula (I) in which the Ar group is mono- or disubstituted according to one of the following formulae:

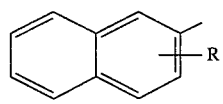
(A)

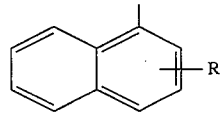
(B)

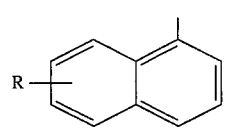
(C)

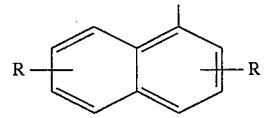
(D)

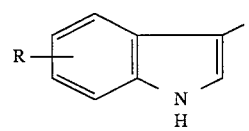
(E)

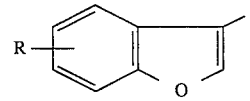
(F)

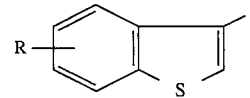
(G)

with R as defined in formula (I).

In a particular manner, the invention relates to the compounds of formula (I) in which the Ar group is mono- or disubstituted according to one of the following formulae:

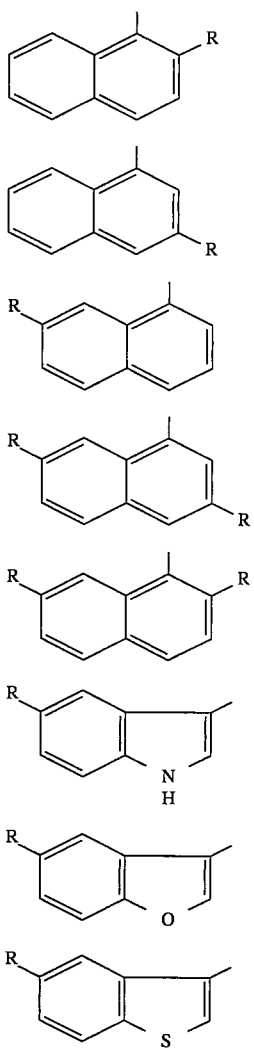

with R as defined in formula (I).

For example, the invention relates to the following compounds:

O-[(7-methoxynaphth-1-yl)methyl]-N-acetylhydroxylamine

O-[(7-methoxynaphth-1-yl)methyl]-N-propionylhydroxylamine

O-[(7-methoxynaphth-1-yl)methyl]-N-cyclopropylcarbonylhydroxylamine

O-[(2-methoxynaphth-1-yl)methyl]-N-acetylhydroxylamine

O-[(2-methoxynaphth-1-yl)methyl]-N-propionylhydroxylamine

O-[(2-methoxynaphth-1-yl)methyl]-N-cyclopropylcarbonylhydroxylamine

O-[(naphth-1-yl)methyl]-N-acetylhydroxylamine

The invention also extends to the process for preparing the compounds of formula (I), in which a compound of formula (II):

$$Ar-CH_2-O-NH-R_1 \quad (II)$$

in which Ar and $R_1$ are as defined in formula (I) is reacted with a compound of formula (III):

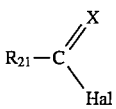

(III)

in which $R_{21}$ and X are as defined in formula (I) and Hal represents a halogen atom, or with the corresponding acid anhydride, or with formic acid, in order to obtain a compound of formula (I'):

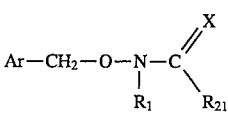

(I')

in which Ar, X, $R_1$ and $R_{21}$ are as defined above, or with a compound of formula (III'):

$$X=C=N-R_{22} \quad (III')$$

in which X and $R_{22}$ are as defined in formula (I) in order to obtain a compound of formula (I"):

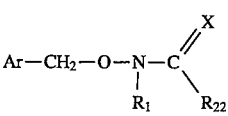

(I")

in which Ar, $R_1$, $R_{22}$ and X are as defined above, the compounds of formulae (I') and (I") forming the set of compounds of formula (I), which compounds of formula (I) are, where appropriate:

purified according to one or more purification methods chosen from crystallization, chromatography, extraction, filtration, and passage over charcoal or resin, or separated, where appropriate, in pure form or in the form of a mixture, into their possible enantiomers or diastereoisomers.

The invention also extends to the process for preparing the compounds of formula (I/a):

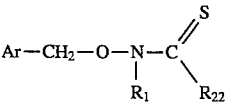

(I/a)

in which Ar, $R_1$ and $R_{22}$ are as defined in formula (I), by reacting a compound of formula (I/b):

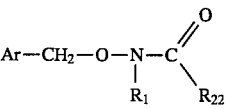

(I/b)

in which Ar, $R_1$ and $R_{22}$ are as defined above, with a thionation reagent, for example with Lawesson's reagent, which compounds of formula (I/a) are, where appropriate:

purified according to one or more purification methods chosen from crystallization, chromatography, extraction, filtration, and passage over charcoal or resin, or separated, where appropriate, in pure form or in the form of a mixture, into their possible enantiomers or diastereoisomers.

The invention also extends to the process for preparing the compounds of formula (I/c):

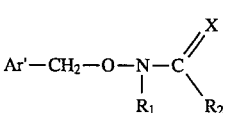

(I/c)

in which X, $R_1$ and $R_2$ are as defined in formula (I) and Ar' represents a group of formula Ar as defined in formula (I)

substituted with at least one radical —CO—Ra, —O—CO—Ra, —OH and —CH₂—Ra,
wherein a compound of formula (I/d):

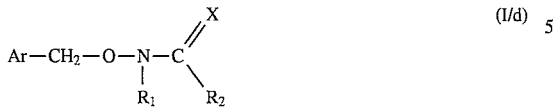

in which Ar is as defined in formula (I) and X, R₁ and R₂ are as defined above, is subjected to a substitution reaction with a compound of formula (IV):

with Ra as defined in formula (I) and Hal representing a halogen, in order to obtain the corresponding compound of formula (I/e):

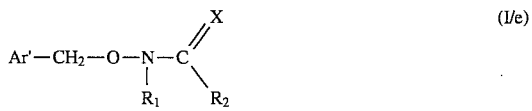

in which Ar', R₁, R₂ and X are as defined above, corresponding to a compound of formula (I/c) in which Ar' is substituted with at least one substituent of formula —CO—Ra, which compound of formula (I/e) is:
either subjected to an oxidation by a Bayer-Villiger reaction, in order to oxidize the substituent —CO—Ra and obtain a compound of formula (I/c) in which Ar' is substituted with at least one substituent of formula —O—CO—Ra,
or subjected to a saponification in order to obtain a compound of formula (I/c) in which Ar' is substituted with at least one substituent —OH,
or subjected to a reduction with mercury and zinc, in the presence of toluene and hydrochloric acid so as to reduce the substituent —CO—Ra to —CH₂—Ra, in order to obtain a compound of formula (I/c) in which Ar' is substituted with at least one substituent —CH₂—Ra,
which compounds of formula (I/c) are, where appropriate:
purified according to one or more purification methods chosen from crystallization, chromatography, extraction, filtration, and passage over charcoal or resin,
or separated, where appropriate, in pure form or in the form of a mixture, into their possible enantiomers or diastereoisomers.

The compounds of formula (I) may also be subjected, if the Ar group has a substituent —OCH₃, to a dimethylation reaction with boron tribromide, in order to obtain the corresponding hydroxyl functional group.

The starting materials used in the process described above are either commercially available, or easily accessible to persons skilled in the art by means of processes known in the literature, or accessible through the preparations described below.

The compounds of formula (I) have very advantageous pharmacological properties.

The compounds of the invention are useful in the prevention and treatment of disorders of the melatoninergic system.

A pharmacological study of the compounds of the invention indeed showed that they were not toxic, were endowed with a very high selective affinity for the melatonin receptors and that they exhibit substantial activity on the central nervous system and in particular, properties on sleep disorders, anxiolytic, antipsychotic and analgesic properties as well as an activity on the circulation were noted which make it possible to establish that the products of the invention are especially useful in the treatment of stress, sleep disorders, anxiety, seasonal depression, insomnia and fatigue due to jet lag, schizophrenia, panic attacks, melancholia, appetite regulation, insomnia, psychotic disorders, epilepsy and Parkinson's disease, senile dementia, various disorders linked to normal or pathological aging, migraine, vascular disorders, memory loss, Alzheimer's disease, as well as cerebral circulation disorders. In another area of activity, it appears that the products of the invention possess inhibitory properties on ovulation, immunomodulatory properties and that they are capable of being used in the treatment of certain hormone-dependent cancers.

The compounds will preferably be used in the treatment of seasonal depression, sleep disorders, cardiovascular pathologies, insomnia and fatigue due to jet lag, appetite disorders and obesity.

For example, the compounds will be used in the treatment of seasonal depression and sleep disorders.

The subject of the present invention is also the pharmaceutical compositions containing at least one compound of formula (I) in combination with one or more pharmaceutically acceptable excipients.

Among the pharmaceutical compositions according to the invention, there may be mentioned, more particularly, those which are suitable for oral, parenteral, nasal, per- or transcutaneous, rectal, perlingual, ocular or respiratory administration and especially plain or sugar-coated tablets, sublingual tablets, sachets, packets, gelatin capsules, glossettes, lozenges, suppositories, creams, ointments, skin gels, and ampoules to be taken orally or injected.

The dosage varies according to the sex, age and weight of the patient, the route of administration, the nature of the therapeutic indication, or the treatments which may be associated and ranges between 0.1 mg and 1 g per 24 hours in 1 or 2 doses, more particularly 1 to 100 mg, for example 1 to 10 mg.

The following examples illustrate the invention, but do not limit it in any manner.

Preparation 1

1-Hydroxymethyl-2-Methoxynaphthalene

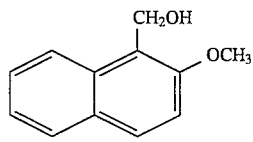

0.11 mole of lithium aluminum hydride (AlLiH₄) is suspended in 400 cm³ of tetrahydrofuran (THF) in a one liter round-bottomed flask surmounted by a reflux condenser.

0.1 mole of commercially available 2-methoxy-1-naphthaldehyde is slowly added, with vigorous stirring.

The mixture is then heated at 40° C. for 30 min and then cooled on an ice bath; a mixture of tetrahydrofuran and water (90/10) is slowly added so as to destroy the complex and the lithium aluminum hydride in excess.

After filtration of the white inorganic precipitate, the organic phase is washed with water and then dried. The solvent is removed under vacuum; the desired alcohol is thus obtained practically pure.

Melting point: 101°–102° C.

Recrystallization solvent: ether-cyclohexane

NMR (CDCl$_3$): 2.15 ppm (singlet, 1H, (—OH))

3.90 ppm (singlet, 3H, (—O—CH$_3$))

5.10 ppm (singlet, 2H, (Ar—CH$_2$—O))

7.20 to 8.20 ppm (unresolved complex, 6H, (aromatic H)).

Preparation 2

1-Acetoxymethyl-7-Methoxynaphthalene

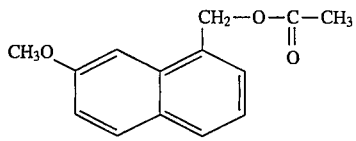

Stage A: ethyl (7-methoxy-1,2,3,4-tetrahydronaphthyliden-1-yl)acetate 50 g of 7-methoxy-1-tetralone, 40 g of ethyl bromoacetate and 150 cm$^3$ of benzene are mixed by means of a dropping funnel. The mixture is added over needle-shaped zinc which is activated (18.6 g) according to Reformatsky and an iodine crystal. The mixture is heated to 60° C. and then refluxed for 45 min.

The resulting mixture is hydrolyzed on ice in the presence of hydrochloric acid, extracted with benzene, dried and heated to boiling temperature in the presence of P$_2$O$_5$. The mixture is filtered and dried.

The residue is used as it is in the next step.

Yield: 80%

Stage B: ethyl (7-methoxynaphth-1-yl)acetate 50 g of ethyl (7-methoxy-1,2,3,4-tetrahydronaphthyliden-1-yl)acetate are mixed with 7.35 g of sulfur and the mixture is heated at 215° C. for 10 hours. The resulting mixture is cooled, 300 cm$^3$ of ethyl acetate are added, the mixture is stirred for 30 min, filtered and dried.

The residue obtained is used as it is for the saponification step.

Stage C: (7-methoxynaphth-1-yl)acetic acid

A mixture of ethyl (7-methoxynaphth-1-yl)acetate obtained above in 250 cm$^3$ of sodium hydroxide at 20% in ethanol is refluxed for 3 hours.

The mixture is dried and the residue is washed with ether. The product is precipitated with a stream of gaseous hydrochloric acid.

Melting point: 155°–156° C.

Yield: 68%

Stage D: 1-acetoxymethyl-7-methoxynaphthalene 0.1 mole of (7-methoxynaphth-1-yl)acetic acid obtained above is dissolved in 200 cm$^3$ of anhydrous benzene and 100 cm$^3$ of anhydrous acetic acid.

The mixture is heated to boiling temperature under an argon stream in order to completely remove the traces of oxygen dissolved in the reaction mixture.

1.1 moles of lead tetraacetate are added at cold temperature and then the very dark reaction mixture is heated slowly, with stirring and under an argon stream. At around 70° C., a substantial emission of CO$_2$ occurs, accompanied by decoloration of the solution. The solvents are then removed under reduced pressure. The residue is taken up in dichloromethane and ether; the inorganic precipitate formed is filtered on celite. The flitrate is successively washed twice with a 5% sodium bicarbonate solution and then with water. The organic phase, dried over Na$_2$SO$_4$, is filtered. The solvents are removed under vacuum, leading to a cream-colored oil consisting of the desired compound practically pure. This oil may be purified by chromatography on silica (eluent CH$_2$Cl$_2$).

The acidification, with concentrated HCl, of the sodium-bicarbonate washings makes it possible to recover the unreacted starting acid (10%).

Yield: 85%

NMR (CDCl$_3$):2.10 ppm (singlet, 3H,

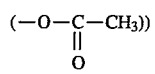

3.90 ppm (singlet, 3H, (—O—CH$_3$)), 5.50 ppm (singlet, 2H, (Ar—CH$_2$—O—)), 7.10 to 7.90 ppm (unresolved complex, 6H, (aromatic H)).

Preparation 3

1-Hydroxymethyl-7-Methoxynaphthalene 0.1 mole of the preceding 1-acetoxymethyl-7-methoxynaphthalene is saponified at room temperature, under argon, with a solution of 0.2 mole of sodium hydroxide diluted in 200 cm$^3$ of methanol and 40 cm$^3$ of water.

The methanol is removed under vacuum and then the residue is poured over ice and acidified with concentrated hydrochloric acid. The residue is extracted with ether. After washing the ethereal phase twice with water, drying over Na2SO$_4$, the ether is removed under reduced pressure, leading to an oil which crystallizes immediately upon cooling.

The desired alcohol is obtained in a practically pure state which melts after recrystallization.

Melting point: 71° C.

NMR (CDCl$_3$): 2.50 ppm (broad singlet, 1H, (—OH)), 3.90 ppm (singlet, 3H, (—O—CH$_3$)), 5.05 ppm (singlet, 2H, (Ar—CH$_2$—O)), 7.10 to 7.85 (unresolved complex, 6H, (aromatic H)).

Preparation 4

1-Chloromethyl-2-Methoxynaphthalene 0.1 mole of 1-hydroxymethyl-2-methoxynaphthalene (preparation 1 ) and 0.11 mole of pyridine are dissolved in 100 cm$^3$ of anhydrous benzene.

The mixture is cooled to 0° C. and then 0.11 mole of thionyl chloride diluted in 50 cm$^3$ of anhydrous benzene is added.

After one hour at room temperature, the reaction mixture is poured over ice and then extracted twice with ether. The combined organic phases are successively washed with an ice-cold solution of sodium bicarbonate and then with water, dried over sodium sulfate and filtered. The flitrate is concentrated under reduced pressure, leading to the chloromethylated compound which is sufficiently pure to be used as it is.

Preparation 5

1-Chlaromethyl-7-Methoxynaphthalene

By carrying out the procedure in the same manner as for the synthesis of the compound of preparation 4, but replacing 1-hydroxymethyl-2-methoxynaphthalene with 1-hydroxymethyl-7-methoxynaphthalene (preparation 3), the title compound is obtained.

Preparation 6

O-[(2-Methoxynaphth-1-yl)Methyl]Hydroxylamine (According to Kasztreiner E. et al. Acta. Chim. Acad. Sci. Hung. 1975, 84 (2), pp 167–180 and Daudon M. et al Bull. Soc. Chim. Fr. 1976, pp 833).

Stage A: 1-(phthalimidooxymethyl)-2-methoxynaphthalene

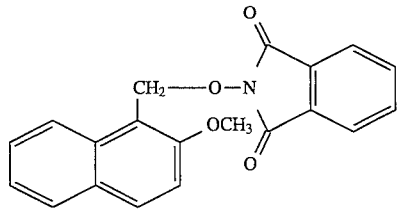

0.1 mole of N-hydroxyphthalimide is dissolved in 60 cm³ of dimethyl sulfoxide (DMSO) and then 0.1 mole of sodium acetate is added, with stirring.

The solution becomes dark red. 0.1 mole of 1-chloromethyl-2-methoxynaphthalene (preparation 4) dissolved in 20 cm³ of DMSO is added all at once and the reaction mixture is heated until decoloration occurs (towards 100° C.) and then cooled. 500 cm³ of chloroform are added and the organic phase is washed twice with a saturated aqueous solution of NaCl.

The organic phase, dried over sodium sulfate, is concentrated under reduced pressure in order to remove the chloroform and the DMSO.

The gummy residue is taken up in ether; the desired compound is obtained in the form of a white precipitate which is chromatographed on silica (eluent $CH_2Cl_2$) in order to remove the traces of the starting N-hydroxyphthalimide.

Melting point: 174° C.
Yield: 80%
NMR ($CDCl_3$): 3.90 ppm (singlet, 3H, (—O—$CH_3$)),
5.80 ppm (singlet, 2H, (Ar—$CH_2$—O—)),
7.20 to 8.50 ppm (unresolved complex, 10 H, (aromatic H)).

Stage B: O-[(2-methoxynaphth-1-yl)methyl]hydroxylamine

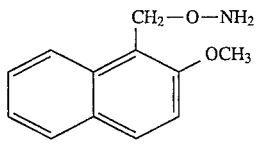

0.01 mole of 1-(phthalimidooxymethyl)-2-methoxynaphthalene, prepared in the preceding stage, and 30 cm³ of ethanol are placed in a round-bottomed flask surmounted by a condenser and then heated to boiling temperature; 0.02 mole of hydrazine hydrate dissolved in 10 cm³ of ethanol is then added all at once. A cottony precipitate of phthalhydrazide forms almost immediately. The boiling is allowed to continue for a further 5 min and then, after cooling, the precipitate is filtered.

The alcoholic solution is concentrated under reduced pressure. The gummy residue, comprising predominantly the title compound, is taken up in 20 cm³ of dichloromethane and filtered. The filtrate is concentrated under vacuum in order to remove the solvent: an oily residue is obtained. Examination of the nuclear magnetic resonance (NMR) spectrum shows that the compound does not require further purification.

NMR (CDCl3): 3.90 ppm (singlet, 3H, (—O—$CH_3$)),
5.25 ppm (singlet, 2H, (aromatic —$CH_2$—O—)),
5.30 ppm (singlet, 2H, (—NH2)),
7.05 to 8.20 ppm (unresolved complex, 6H, (aromatic H)).

Preparation 7

O-[(7-Methoxynaphth-1-yl)Methyl]Hydroxylamine

By carrying out the procedure in the same manner as for the synthesis of the compound of preparation 6, but replacing, at stage A, 1-chloromethyl-2methoxynaphthalene with 1-chloromethyl-7-methoxynaphthalene (preparation 5), the title compound is obtained.

Stage A: 1-(phthalimidooxymethyl)-7-methoxynaphthalene
White crystals
Melting point :202° C.
Yield :90%
NMR ($CDCl_3$): 4.05 ppm (singlet, 3H, (—$OCH_3$)),
5.50 ppm (singlet, 2H, (Ar—$CH_2$—O)),
7.10 to 8.10 ppm (unresolved complex, 10H, (aromatic H)).

Stage B: O-[(7-methoxynaphth-1-yl)methyl]hydroxylamine
NMR ($CDCl_3$): 1.85 ppm (singlet, 3H, (—$COCH_3$)),
3.95 ppm (singlet, 3H, (—$OCH_3$)),
5.30 ppm (singlet, 2H, (Ar—$CH_2$—O)),
7.10 to 7.80 ppm (unresolved complex, 6H, (aromatic H)),
8.45 ppm (singlet, 1H, (NH)).

Preparation 8

O-[(5-Methoxybenzothiophen-3-yl)Methyl]Hydroxylamine

By carrying out the procedure in the same manner as for the synthesis of the compounds of preparations 2 (stage D), 3, 5 and 7, but replacing the starting material, that is to say the (7-methoxynaphth-1-yl)acetic acid with (5-methoxybenzothiophen-3-yl)acetic acid (J. Med. Chem. 1970, 13 (6), pp 1205–1208) the title compound is obtained.

Preparation 9

O-[(5-Methoxybenzofuran-3-yl)Methyl]Hydroxylamine

By carrying out the procedure in the same manner as for the synthesis of the compounds of preparations 2 (stage D), 3, 5 and 7, but replacing the starting material, that is to say the (7-methoxynaphth-1-yl)acetic acid with (5-methoxybenzofuran-3-yl)acetic acid (Zh. Org. Khim. 1967, 3(12), pp 2185–2188) the title compound is obtained.

Preparation 10

O-[(5-Methyoxyindol-3-yl)Methyl]Hydroxylamine

By carrying out the procedure in the same manner as for the synthesis of the compounds of preparations 2 (stage D), 3, 5 and 7, but replacing the starting material, that is to say the (7-methoxynaphth-1-yl)acetic acid with (5-methoxyindol-3-yl)acetic acid, the title compound is obtained.

EXAMPLE 1

O-[(7-Methoxynaphth-1-yl)Methyl]-N-Acetylhydroxylamine

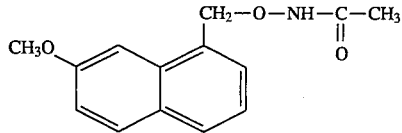

0.01 mole of O-[(7-methoxynaphth-1-yl)methyl]hydroxylamine, obtained from preparation 7, is dissolved in 50 cm³ of chloroform; 30 cm³ of water and 0.02 mole of $K_2CO_3$ are added. 0.012 mole of acetic acid chloride (or acetic anhydride) is then added, with vigorous stirring, at 0° C. After 15 min at 0° C., 10 cm³ of an aqueous $NH_4OH$ solution is added (so as to destroy the excess acid chloride or acetic anhydride), followed by a further 100 cm³ of water. The organic phase is decanted off, washed twice with water and then dried over sodium sulfate. The solvent is evaporated under reduced pressure. The residue, consisting of the title compound, is recrystallized from ether/dichloromethane. Colorless crystals are thus obtained.

Melting point: 125° C.

Yield: 90%

Recrystallization solvent: dichloromethane-ether

NMR ($DCCl_3$): 1.85 ppm (singlet, 3H, (—CO—CH$_3$)), 3.95 ppm (singlet, 3H, (—O—CH$_3$)), 5.30 ppm (singlet, 2H, (Ar—CH$_2$—O—)), 7.10 to 7.80 ppm (unresolved complex, 6H, (aromatic H)), 8.45 ppm (singlet, 1H, (NH)).

EXAMPLE 2

O-[(7-Methoxynaphth-1-yl)Methyl]-N-Propionylhydroxylamine

By carrying out the procedure in the same manner as for the synthesis of the compound of Example 1, but replacing, during the acylation, the acetic acid chloride with propionic acid chloride, the title compound is obtained.

EXAMPLE 3

O-[(7-Methoxynaphth-1-yl)Methyl]-N-Butyrylhydroxylamine

By carrying out the procedure in the same manner as for the synthesis of the compound of Example 1, but replacing, during the acylation, the acetic acid chloride with butyric acid chloride, the title compound is obtained in the form of white crystals.

Melting point: 98° C.

Recrystallization solvent: ether/cyclohexane

NMR ($DCCl_3$): 0.95 ppm (triplet (J=7 Hz), 3H, (—CH$_2$—CH$_2$—CH$_3$)), 1.75 ppm (poorly resolved multiplet, 2H, (—CH$_2$—CH$_2$—CH$_3$)), 2.10 ppm (poorly resolved triplet, 2H, (—CH2—CH$_2$—CH$_3$)), 4.00 ppm (singlet, 3H, (—O—CH$_3$)), 7.15 to 7.85 ppm (unresolved complex, 6H (aromatic H)).

8.20 ppm (singlet, 1H, (NH)).

EXAMPLE 4

O-[(7-Methoxynaphth-1-yl)Methyl]-N-Crotonyl-Hydroxylamine

By carrying out the procedure in the same manner as for the synthesis of the compound of Example 1, but replacing, during the acylation, the acetic acid chloride with crotonic acid chloride, the title compound is obtained.

EXAMPLE 5

O-[(7-Methoxynaphth-1-yl)Methyl]-N-Iodoacetyl-Hydroxylamine

By carrying out the procedure in the same manner as for the synthesis of the compound of Example 1, but replacing, during the acylation, the acetic acid chloride with iodoacetic acid chloride, the title compound is obtained.

EXAMPLE 6

O-[(7-Methoxynaphth-1-yl)Methyl]-N-Cyclopropylbarbonyl-Hydroxylamine

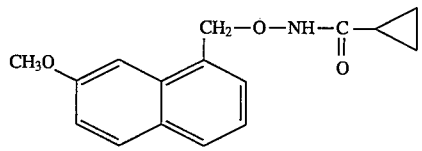

By carrying out the procedure in the same manner as for the synthesis of the compound of Example 1, but replacing, during the acylation, the acetic acid chloride with cyclopropanecarboxylic acid chloride, the title compound is obtained.

Melting point: 126° C.

Recrystallization solvent: cyclohexane

Colorless crystals

NMR (CDCl3): 0.65 to 1.20 ppm (unresolved complex, 5H, (cyclopropane H)), 3.95 ppm (singlet, 3H, (O—CH$_3$)), 5.30 ppm (singlet, 2H, (Ar—CH$_2$—O—)), 7.15 to 7.80 ppm (unresolved complex, 5H, (aromatic H)), 8.40 ppm (singlet 1H, (—NH)).

EXAMPLE 7

O-[(2-Methoxynaphth-1-yl)Methyl]-N-Acetylhydroxylamine

By carrying out the procedure in the same manner as for the synthesis of the compound of Example 1, but using the O-[(2-methoxynaphth-1-yl)methyl]hydroxylamine of preparation 6, the title compound is obtained.

Melting point: 112° C.

Recrystallization solvent: ether/dichloromethane

Colorless crystals

NMR (CDCl$_3$): 1.9 ppm (singlet, 3H, (—CO—CH$_3$)), 3.95 ppm (singlet,3 2H, (—O—CH$_3$)), 5.45 ppm (singlet, 2H, (Ar—CH$_2$—O)), 7.10 to 8.40 ppm (unresolved complex, 6H, (aromatic H)), 8.50 ppm (singlet 1H, (NH)).

EXAMPLE 8

O-[(2-Methoxynaphth-1-yl)Methyl]-N-Propionyl-Hydroxylamine

By carrying out the procedure in the same manner as for the synthesis of the compound of Example 7, but replacing, in the acylation step, the acetic acid chloride with propionic acid chloride, the title compound is obtained.

Melting point: 118° C.

Recrystallization solvent: ether

Colorless crystals

NMR (DCCl$_3$): 1.15 ppm (poorly resolved triplet, 3H, (—CH$_2$—C$\underline{H}_3$)), 1.9 to 2.5 ppm (unresolved complex, 2H, (—C$\underline{H}_2$—CH$_3$)), 3.90 ppm (singlet, 3H, (—O—CH$_3$)), 5.50 ppm (singlet, 2H, (Ar—CH$_2$—O—)), 7.10 to 8.40 ppm (unresolved complex, 6H, (aromatic H)), 8.80 ppm (singlet 1H, (NH)).

EXAMPLE 9

O-[(2-Methoxynaphth-1-yl)Methyl]-N-Butyrylhydroxylamine

By carrying out the procedure in the same manner as for the synthesis of the compound of Example 7, but replacing, in the acylation step, acetic acid chloride with butyric acid chloride, the title compound is obtained.

EXAMPLE 10

O-[(2-Methoxynaphth-1-yl)Methyl]-N-Crotonyl-Hydroxylamine

By carrying out the procedure in the same manner as for the synthesis of the compound of Example 7, but replacing, in the acylation step, acetic acid chloride with crotonic acid chloride, the title compound is obtained.

EXAMPLE 11

O-[(2-Methoxynaphth-1-yl-Methyl]-N-Iodoacetyl-Hydroxylamine

By carrying out the procedure in the same manner as for the synthesis of the compound of Example 7, but replacing, in the acylation step, acetic acid chloride with iodoacetic acid chloride, the title compound is obtained.

EXAMPLE 12

O-[(2-Methoxynaphth-1-yl)Methyl]-N-Cyclopropylcarbonylhydroxylamine

By carrying out the procedure in the same manner as for the synthesis of the compound of Example 7, but replacing, in the acylation step, the acetic acid chloride with cyclopropanecarboxylic acid chloride, the title compound is obtained.

Melting point: 145° C.

Recrystallization solvent: ether

Colorless crystals

NMR (CDCl$_3$): 0.51 to 1.30 ppm (multiplets, 5H, (cyclopropane H)), 3.95 ppm (singlet, 3H, (—O—CH$_3$)), 5.50 ppm (singlet, 2H, (Ar—CH$_2$—O)), 7.10 to 8.20 ppm (unresolved complex, 6H, (aromatic H)), 8.40 ppm (singlet, 1H (NH))).

EXAMPLE 13

O-[(5-Methoxyindol-3-yl)Methyl]-N-Acetylhydroxylamine

By carrying out the procedure in the same manner as for the synthesis of the compound of Example 1, but replacing 0-[(7-methoxynaphth-1-yl)methyl]hydroxylamine with O-[5-methoxyindol-3-yl)methyl]hydroxylamine (preparation 10), the title compound is obtained.

EXAMPLE 14

O-[(5-Methoxyindol-3-yl)Methyl]-N-Propionyl-Hydroxylamine

By carrying out the procedure in the same manner as for the synthesis of the compound of Example 13, but replacing, in the acylation step, the acetic acid chloride with propionic acid chloride, the title compound is obtained.

EXAMPLE 15

O-[(5-Methoxyindol-3-yl)]-N-Butyrylhydroxylamine

By carrying out the procedure in the same manner as for the synthesis of the compound of Example 13, but replacing, in the acylation step, the acetic acid chloride with butyric acid chloride, the title compound is obtained.

EXAMPLE 16

O-[(5-Methoxyindol-3-yl)Methyl]-N-Crotonyl-Hydroxylamine

By carrying out the procedure in the same manner as for the synthesis of the compound of Example 13, but replacing the acetic acid chloride with crotonic acid chloride, the title compound is obtained.

EXAMPLE 17

O-[(5-Methoxyindol-3-yl)Methyl]-N-Iodoacetyl-Hydroxylamine

By carrying out the procedure in the same manner as for the synthesis of the compound of Example 13, but replacing the acetic acid chloride with iodoacetic acid chloride, the title compound is obtained.

EXAMPLE 18

O-[( 5-Methoxyindol-3-yl)Methyl]-N-Cyclo-Propylcarbonylhydroxylamine

By carrying out the procedure in the same manner as for the synthesis of the compound of Example 13, but replacing the acetic acid chloride with cyclopropanecarboxylic acid chloride, the title compound is obtained.

EXAMPLE 19

O-[(5-Methoxybenzothiophen-3-yl)Methyl]-N-Acetylhdroxylamine

By carrying out the procedure in the same manner as for Example 1, but replacing O-[(7-methoxynaphth- 1-yl)methyl]hydroxylamine with O-[(5-methoxybenzothiophen-3-yl)methyl]hydroxylamine (Preparation 8), the title compound is obtained.

EXAMPLE 20

O-[(5-Methoxybenzothiophen-3-yl)Methyl]-N-Propionylhydroxylamine

By carrying out the procedure in the same manner as for the synthesis of the compound of Example 19, but replacing, in the acylation step, the acetic acid chloride with propionic acid chloride, the title compound is obtained.

EXAMPLE 21

O-[(5-Methoxybenzofuran-3-yl)Methyl]-N-Acetyl-Hydroxylamine

By carrying out the procedure in the same manner as for the synthesis of the compound of Example 1, but replacing O-[(7-methoxynaphth-1-yl)methyl]hydroxylamine with O-[(5-methoxybenzofuran-3-yl)methyl]hydroxylamine (preparation 9), the title compound is obtained.

EXAMPLE 22

O-[(5-Methoxybenzofuran-3-yl)Methyl]-N-Butryl-Hydroxylamine

By carrying out the procedure in the same manner as for the synthesis of the compound of Example 21, but replacing, in the acylation step, the acetic acid chloride with butyric acid chloride, the title compound is obtained.

EXAMPLE 23

O-[(5-Methoxybenzofuran-3-yl)Methyl]-N-Cyclopropyl-Carbonylhydroxylamine

By carrying out the procedure in the same manner as for the synthesis of the compound of Example 21, but replacing, in the acylation step, the acetic acid chloride with cyclopropanecarboxylic acid chloride, the title compound is obtained. EXAMPLES 24 to 50

By carrying out the procedure in the same manner as for the synthesis of the preceding compounds, but using the appropriate reagents, the compounds of Examples 24 to 50 are obtained.

In order to synthesize the compounds having a urea or thiourea on the nitrogen of the hydroxylamine, the procedure is carried out by reacting an alkyl, cycloalkyl or alkylcycloalkyl isocyanate or isothiocyanate as defined in formula (I) with a suspension of preparations 6 to 10.

EXAMPLE 24

O-[(5-Methoxyindol-3-yl)Methyl]-N-Trifluoroacetyl-Hydroxylamine

EXAMPLE 25

N-[(5-Methoxyindol-3-yl)Methyloxy]-N'-Propylurea

EXAMPLE 26

N-[(5-Methoxyindol-3-yl)Methyloxy]-N'-Butylurea

EXAMPLE 27

O-[(7-Methoxynaphth-3-yl)Methyl]-N-Trifluoroacetyl-Hydroxylamine

EXAMPLE 28

O-[(7-Methoxynaphth-1-yl)Methyl]-N-Cyclobutylcarbonyl-Hydroxylamine

EXAMPLE 29

N-[(7-Methoxynaphth-1-yl)Methyloxy]-N'-Propylurea

EXAMPLE 30

N-[(7-Methoxynaphth-1-yl)Methyloxy]-N'-Butylurea

EXAMPLE 31

N-[(7-Methoxynaphth-1-yl)Methyloxy]-N'-Methylurea

EXAMPLE 32

O-[(3-Acetyl-7-Methoxynaphth-1-yl)Methyl]-N-Acetyl-Hydroxylamine

Starting with a solution of the compound of Example 1 and AlCl$_3$, in a solvent such as nitrobenzene, acetyl chloride is added dropwise at 12° C. and under nitrogen. The reaction is allowed to proceed for 2 hours at 12° C. and the reaction mixture is poured over ice. The crude mixture is extracted, dried, concentrated and chromatographed on silica. The title compound is obtained.

EXAMPLES 33 to 35

By carrying out the procedure as in Example 32, but using the appropriate acyl chlorides, the compounds of the following examples are obtained:

EXAMPLE 33

O-[(3-Propionyl-7-Methoxynaphth-1-yl)MethyL]-N-Acetyl-Hydroxylamine

EXAMPLE 34

O-[(3-Cyclopropylcarbonyl-7-Methoxynaphth-1-yl)Methyl]-N-Acetylhydroxylamine

EXAMPLE 35

O-[(3-Benzyl-7-Methoxynaphth-1-yl)Methyl]-N-Acetyl-Hydroxylamine

EXAMPLE 36

O-(3-Ethyl-7-Methoxynaphth-1-yl)-N-Acetylhydroxylamine

Starting with a solution of 72 mg of mercuric chloride in 5.5 cm$^3$ of water, 3.6 g of zinc powder are added. The mixture is stirred for 30 min. It is allowed to separate and the water is removed.

3.6 cm$^3$ of water are then added to this amalgam, followed by 3.6 cm$^3$ of concentrated hydrochloric acid and then 5.26 mmol of the compound prepared according to Example 32, and 25 cm$^3$ of toluene.

The mixture is refluxed for 2 h, the organic phase is extracted, washed with water and, after drying over magnesium sulfate, filtered and evaporated to dryness. The title compound is thus obtained.

EXAMPLES 37 to 39

By carrying out the procedure as in Example 36, but starting with Examples 33 to 35, the compounds of the following examples are obtained:

EXAMPLE 37

O-[(3-Propyl-7-Methoxynaphth-1 -yl)]-N-Acetyl Hydroxylamine

EXAMPLE 38

O-[(3-Cyclopropylmethyl-7-Methoxy)Methyl)]-N-Acetyl Hydroxylamine

EXAMPLE 39

O-[(3-Benzyl-7-Methoxynaphth-1-yl)Methyl]-N-Acetyl Hydroxylamine

EXAMPLES 40 to 105

By carrying out the procedure as in the preceding examples, but using the appropriate reagents, the compounds of the following examples are obtained:

EXAMPLE 40

O-[(3-Ethyl-7-Methoxynaphth-1-yl]-N-Cyclopropyl Carbonylhydroxylamine

EXAMPLE 41

N-[(7-Methoxynaphth-1-yl)Methyloxy]-N'-Propylthiourea

EXAMPLE 42

N-[(7-Methoxynaphth-1-yl)Methyloxy]-N'-Butylthiourea

EXAMPLE 43

N-[(7-Methoxynaphth-1-yl)Methyloxy]-N'-Methylthiourea

EXAMPLE 44

N-[(5-Methoxybenzothiophen-3-yl)Methyloxy]-N'-Methyl Thiourea

EXAMPLE 45

O-[(5-Methoxybenzothiophen-3-yl)Methyl]-N-Thiopropionyl Hydroxylamine

EXAMPLE 46

N-[(5-Methoxybenzothiophen-3-yl)Methyloxy]-N'-Propyl Thiourea

EXAMPLE 47

O-[(5-Methoxybenzofuran-3-yl)Methyl]-N-Thioacetyl Hydroxylamine

EXAMPLE 48

N-[(5-Methoxybenzofuran-3-yl)Methyloxy]-N'-Methyl Thiourea

EXAMPLE 49

N-[(5-Methoxybenzofuran-3-yl)Methyloxy]-N'-Propyl Thiourea

EXAMPLE 50

N-[(5-Methoxybenzofuran-3-yl)Methyl]-N'-Cyclopropyl Thiourea

EXAMPLE 51

O-[(3-Acetylnaphth-1-yl)Methyl]-N-Acetylhydroxylamine

EXAMPLE 52

O-[(3-Cyclopropionylnaphth-1-yl)Methyl]-N-Acetyl Hydroxylamine

EXAMPLE 53

O-[(3-Benzoylnaphth-1-yl)Methyl]-N-Acetylhydroxylamine

EXAMPLE 54

O-[(3-Benzylnaphth-1-yl)Methyl]-N-Acetylhydroxylamine

EXAMPLE 55

O-[(3-Ethylnaphth-1-yl)Methyl]-N-Acetylhydroxylamine

EXAMPLE 56

O-[(3-Acetoxy-7-Methoxynaphth-1-yl)Methyl]-N-Acetyl Hydroxylamine

A solution of 12.3 mmol of the magnesium salt of monoperoxyphthalic acid in 100 cm³ of water, adjusted to pH 5 with 1N NaOH, is added to a solution of 9.81 mmol of the compound of Example 32 in 125 cm³ of methanol. The mixture is stirred at room temperature for 24 hours. The methanol is evaporated, 1N NaHCO₃ added and the mixture is extracted with CH₂Cl₂, dried over MgSO₄, filtered and concentrated. The title compound is obtained.

EXAMPLE 57

O-[(3-Hydroxy-7-Methoxynaphth-1-yl)Methyl]-N-Acetyl Hydroxylamine

The residue obtained in Example 56 is dissolved in 200 cm³ of methanol and treated with 250 cm³ of 0.05N NaOH for 1 hour at room temperature. The methanol is evaporated and the mixture is adjusted to pH 12 with 1N NaOH, extracted with CH₂Cl₂, dried over MgSO₄, filtered and concentrated. After chromatography on silica, the title compound is obtained.

EXAMPLE 58

O-[(7-Ethoxynaphth-1-yl)Methyl]-N-Acetylhydroxylamine

EXAMPLE 59

O-[(7-Propoxynaphth-1-yl)Methyl]-N-Acetylhydroxylamine

EXAMPLE 60

O-[(7-Ethylnaphth-1-yl)Methyl]-N-Acetylhydroxylamine

EXAMPLE 61

O-[(Naphth-1-yl)Methyl]-N-Acetylhydroxylamine

EXAMPLE 62

O-[(7-Ethoxynaphth-1-yl)Methyl]-N-Cyclopropylcarbonyl Hydroxylamine

EXAMPLE 63

O-[(7-Propoxynaphth-1-yl)Methyl]-N-Cyclopropyl Carbonylhydroxylamine

EXAMPLE 64

O-[(7-Ethylnaphth-1-yl)Methyl]-N-Cyclopropylcarbonyl Hydroxylamine

EXAMPLE 65

O-[(Naphth-1-yl)Methyl]-N-Cyclopropylcarbonyl-Hydroxylamine

EXAMPLE 66

O-[(Naphth-1-yl)Methyl]-N-Cyclobutylcarbonyl Hydroxylamine

EXAMPLE 67

O-[(2-Ethoxynaphth-1-yl)Methyl]-N-Acetylhydroxylamine

EXAMPLE 68

O-[(2-Propoxynaphth-1-yl)Methyl]-N-Acetylhydroxylamine

EXAMPLE 69

O-[(2-Ethylnaphth-1-yl)Methyl]-N-Acetylhydroxylamine

EXAMPLE 70

O-[(2-Ethoxynaphth-1-yl)Methyl]-N-Cyclopropylcarbonyl Hydroxylamine

EXAMPLE 71

O-[(2-Propoxynaphth-1-yl)Methyl]-N-Cyclopropyl Carbonylhydroxylamine

EXAMPLE 72

O-[(2-Ethylnaphth-1-yl)Methyl]-N-Cyclopropylcarbonyl Hydroxylamine

EXAMPLE 73

O-[(2-Ethylnaphth-1-yl)Methyl]-N-Cyclobutylcarbonyl Hydroxylamine

EXAMPLE 74

O-[(5-Ethoxyindol-3-yl)Methyl]-N-Acetylhydroxylamine

EXAMPLE 75

O-[(5-Propoxyindol-3-yl)Methyl]-N-Acetylhydroxylamine

EXAMPLE 76

O-[(5-Ethylindol-3-yl)Methyl]-N-Acetylhydroxylamine

EXAMPLE 77

O-[(Indol-3-yl)Methyl]-N-Acetylhydroxylamine

EXAMPLE 78

O-[(5-Ethoxyindol-3-yl)Methyl]-N-Cyclopropylcarbonyl Hydroxylamine

EXAMPLE 79

O-[(5-Propoxyindol-3-yl)Methyl]-N-Cyclopropylcarbonyl Hydroxylamine

EXAMPLE 80

O-[(5-Ethylindol-3-yl)Methyl]-N-Cyclopropylcarbonyl Hydroxylamine

EXAMPLE 81

O-[(Indol-3-yl)Methyl]-N-Cyclopropylcarbonyl Hydroxylamine

EXAMPLE 82

O-[(Indol-a-yl)Methyl]-N-Cyclobutylcarbonyl Hydroxylamine

EXAMPLE 83

O-[(5-Ethoxybenzothiophen-3-yl)Methyl]-N-Acetyl Hydroxylamine

EXAMPLE 84

O-[(5-Propoxybenzothiophen-3-yl)Methyl]-N-Acetyl Hydroxylamine

EXAMPLE 85

O-[(5-Ethylbenzothiophen-3-yl)Methyl]-N-Acetyl Hydroxylamine

EXAMPLE 86

O-[(Benzothiophen-3-yl)Methyl]-N-Acetylhydroxylamine

EXAMPLE 87

O-[(5-Ethoxybenzothiophen-3-yl)Methyl]-N-Cyclopropyl Carbonylhydroxylamine

EXAMPLE 88

O-[(5-Propoxybenzothiophen-3-yl)Methyl]-N-Cyclopropyl Carbonylhydroxylamine

EXAMPLE 89

O-[(5-Ethylbenzothiophen-3-yl)Methyl]-N-Cyclopropyl Carbonylhydroxylamine

EXAMPLE 90

O-[(Benzothiophen-3-yl)Methyl]-N-Cyclopropylcarbonyl Hydroxylamine

EXAMPLE 91

O-[(Benzothiophen-3-yl)Methyl]-N-Cyclobutylcarbonyl Hydroxylamine

EXAMPLE 92

O-[(5-Ethoxybenzofuran-3-yl)Methyl]-N-Acetyl Hydroxylamine

EXAMPLE 93

O-[(5-Propoxybenzofuran-3-yl)Methyl]-N-Acetyl Hydroxylamine

EXAMPLE 94

O-[(5-Ethylbenzofuran-3-yl)Methyl]-N-Acetyl Hydroxylamine

EXAMPLE 95

O-[(Benzofuran-3-yl)Methyl]-N-Acetylhydroxylamine

EXAMPLE 96

O-[(5-Ethoxybenzofuran-3-yl)Methyl]-N-Cyclopropyl Carbonylhydroxylamine

EXAMPLE 97

O-[(5-Propoxybenzofuran-3-yl)Methyl]-N-Cyclopropyl Carbonylhydroxylamine

EXAMPLE 98

O-[(5-Ethylbenzofuran-3-yl)Methyl]-N-Cyclopropyl Carbonylhydroxylamine

EXAMPLE 99

O-[(Benzofuran-3-yl)Methyl]-N-Cyclopropylcarbonyl Hydroxylamine

EXAMPLE 100

O-[(Benzofuran-3-yl)Methyl]-N-Cyclobutylcarbonyl Hydroxylamine

EXAMPLE 101

O-[(2,7-Dimethoxynaphth-1-yl)Methyl]-N-Acetyl Hydroxylamine

EXAMPLE 102

O-[(2,7-Dimethoxynaphth-1-yl)Methyl]-N-Cyclopropyl Carbonylhydroxylamine

EXAMPLE 103

O-[(2,7-Dimethoxynaphth-1-yl)Methyl]-N-Trifluoro Acetylhydroxylamine

EXAMPLE 104

O-[(2,7-Dimethoxynaphth-1-yl)Methyl]-N-Propionyl Hydroxylamine

EXAMPLE 105

O-[(2,7-Dimethoxynaphth-1-yl)Methyl]-N-Cyclobutyl Carbonylhydroxylamine

Pharmacological Study of the Compounds of the Invention

EXAMPLE A

Acute Toxicity Study

Acute toxicity was assessed after oral administration to lots of 8 mice (26±2 grams). The animals were observed at regular intervals during the first day and daily during the two weeks following the treatment. The lethal dose 50 (LD 50), which causes the death of 50% of the animals, was evaluated.

The LD 50 of the products tested is greater than 1000 mg.kg$^{-1}$ for the compounds studied, which indicates the low toxicity of the compounds of the invention.

EXAMPLE B

Four-Plate Test

The products of the invention are administered via the esophageal route 30 minutes after the administration of the products to be studied, the animals are placed in compartments, the floor of which comprises four metal plates. Each time the animal passes from one plate to another, it receives a slight electric shock (0.35 mA). The number of passes is recorded for one minute. After administration, the compounds of the invention significantly increase the number of passes, which shows the anxiolytic activity of the compounds of the invention.

EXAMPLE C

Activity of the Products of the Invention on Ischemic Microcirculation

The experimental study was performed on the cremaster muscles of male rats (Sprague-Dawley) after ligating the common iliac artery.

The muscles were placed in a transparent chamber, perfused with a bicarbonate buffer solution equilibrated with a gaseous mixture $CO_2/N_2$ 5/95%. The velocity of the red blood cells and the diameter of the first or second order arterioles irrigating the cremaster were measured, and the arteriolar blood flow was calculated. Identical information was obtained for four types of veinlets.

The same type of measurement was performed simultaneously:
on the cremaster perfused normally,
on the cremaster after ligation, that is to say the cremaster made ischemic 2, 7, 14 and 21 days after ligation.
Two groups of animals were studied:
a control group with no treatment,
a group treated by os with a product of the invention, at the rate of 0.1 $mg.kg^{-1}$ per day.

No difference was observed in the velocity of the red blood cells or in the diameter of the vessels in the cremaster muscles normally irrigated in the treated animals compared with the controls.

On the other hand, in the cremaster muscle made ischemic, the mean diameter of the arterioles was enhanced in the treated animals compared with the controls. The velocity of the red blood cells was normalized by a treatment of 21 days.

In fact, in the treated animals, the velocity of the red blood cells and the blood flow rate measured 7 days after the ligation show no significant difference compared with the values obtained in the non-ischemic cremaster. These results are obtained without modifying the blood pressure.

These results indicate that chronic treatment with a compound of the invention enhances microcirculation and blood irrigation of the regions made ischemic.

EXAMPLE D

Stimulation of the Immune Responses

Sheep red blood cells were administered to groups of six mice. These groups of mice were then treated subcutaneously with the compounds of the invention for six days and a control group was treated with a placebo. The mice were then allowed to rest for four weeks and then they received a booster injection of sheep red blood cells without receiving another administration of the product of the invention. The immune response was evaluated 3 days after the booster injection. It is statistically increased in the group treated with the compounds of the invention.

EXAMPLE E

Inhibition of Ovulation

Adult female rats with regular cycles of four days are used.

Daily vaginal smears were prepared and rats were selected after showing at least two consecutive cycles of four days.

Each cycle consists of two days of diestrus, one day of proestrus and one day of estrus.

In the afternoon of the day of proestrus, the lutenizing hormone is released into the blood by the hypophysis. This hormone induces ovulation which results in the presence of eggs in the oviduct on the day of estrus.

The compounds of the invention are administered orally at midday on the day of estrus. The treated and control rats are sacrificed on the day of estrus. The oviducts are examined. A significant percentage decrease is noted in the number of eggs in the oviducts of the treated rats.

EXAMPLE F

Demonstration of the Analgesic Activity

The activity on pain was evaluated in mice (23–25 g) according to a procedure derived from the technique described by SIEGMUND (SIEGMUND E.A., R.A. CADMUS & GOLU, J. Pharm. Exp. Ther. 1954, 119, 1874). The mice, divided by randomization into lots of 12 animals, received the treatment orally (excipient for the controls) 1 hour before the intraperitoneal injection of an aqueous-alcoholic solution of phenyl-p-benzoquinone (Sigma) at 0.02%. The stretchings are counted between the 5th and 10th min after the injection.

It appeared that the compounds of the invention possess an analgesic activity.

EXAMPLE G

Study of Binding to the Melatonin Receptors

B1) Study on Sheep Pars Tuberalis Cells

The studies of binding of the compounds of the invention to the melatonin receptors were performed according to conventional techniques on sheep par tuberalis cells. The pars tuberails of the adenohypophysis is indeed characterized, in mammals, by a high density of melatonin receptors (Journal of Neuroendocrinology 1989, 1, pp 1–4).

Procedure

1) The membranes of sheep pars tuberalis are prepared and used as target tissue in saturation experiments in order to determine the binding capacities and affinities for 2-$[^{125}I]$ iodomelatonin.

2) The membranes of sheep pars tuberails are used as target tissue, with the different compounds to be tested, in competitive binding experiments in relation to melatonin.

Each experiment is performed in triplicate and a range of different concentrations is tested for each compound.

The results make it possible to determine, after statistical analysis, the binding affinities of the compound tested.

Results

It appears that the compounds of the invention possess a high affinity for the melatonin receptors, greater than that of melatonin itself.

B2) Study on the Membranes of Chicken (*Gallus domesticus*) Brain Cells

The animals used are 12-day old chickens (*Gallus domesticus*). They are sacrificed between 13 and 17 hours on the day of their arrival. The brains are rapidly removed and frozen at −200° C. and then stored at −80° C. The membranes are prepared according to the method described by Yuan and Pang (Journal of Endocrinology 1991, 128, pp 475–482). The [$^{125}$I]melatonin is incubated in the presence of the membranes in a buffered solution at pH 7.4 for 60 min at 25° C. At the end of this period, the membrane suspension is filtered (Whatman GF/C). The radioactivity retained on the filter is determined with the aid of a Beckman®LS 6000 liquid scintillation counter.

The products used are:
2-[$^{125}$I]melatonin
melatonin
standard products
original molecules In primary screening, the molecules are tested at 2 concentrations ($10^{-7}$ and $10^{-5}$M). Each result is the mean of 3 independent measurements. The active molecules selected based on the primary screening results were subjected to a quantitative determination of their efficacy (IC$_{50}$). They are used at 10 different concentrations.

Thus, the IC$_{50}$ values found for the preferred compounds of the invention, which correspond to the affinity values, show that the binding of the compounds tested to the melatoninergic receptors is very high.

EXAMPLE H

Study of the Activity of the Compounds of the Invention on the Circadian Rhythms of Rat Locomotor Activity The involvement of melatonin in the occurrence, by day/night alternation, of most physiological, biochemical and behavioral circadian rhythms made it possible to establish a pharmacological model for the search for melatoninergic ligands.

The effects of the molecules are tested on numerous parameters and in particular on the circadian rhythms of locomotor activity which represent a reliable marker of the activity of the endogenous circadian clock.

In this study, the effects of such molecules are evaluated on a specific experimental model, namely rats placed in temporal isolation (permanent darkness).

Procedure

One-month old Long Evans male rats are subjected, on their arrival at the laboratory, to a light cycle of 12 h of light per 24 h (LD 12:12).

After 2 to 3 weeks of adaptation, they are placed in cages equipped with a wheel linked to a recording system so as to detect the phases of locomotor activity and thus to monitor the nychthemeral rhythms (LD) or circadian rhythms (DD).

As soon as the recorded rhythms indicate a stable generation by the LD 12:12 light cycle, the rats are placed in permanent darkness (DD).

Two to three weeks later, when the free course (rhythms reflecting that of the endogenous clock) is clearly established, the rats receive a daily administration of the molecule to be tested.

The observations are performed by visualizing the rhythms of activity:
generation of the rhythms of activity by the light rhythm,
disappearance of the generation of the rhythms in permanent darkness,
generation by the daily administration of the molecule; transient or durable effect.

A software makes it possible:
to measure the duration and the intensity of the activity, the period of the rhythm in the animals in free mode and during the treatment,
to demonstrate, where appropriate, by spectral analysis the existence of circadian and non-circadian (for example ultradian) components.

Results

It appears clearly that the compounds of the invention make it possible to act in a potent manner on the circadian rhythm via the melatoninergic system.

EXAMPLE I

Antiarrhythmic Activity

Procedure (Ref: LAWSON J.W. et al. J. Pharmacol. Expert. Therap. 1968, 160, pp 22–31)

The substance tested is administered intraperitoneally to a group of 3 mice 30 min before exposure to a chloroform anesthetic. The animals are then observed for 15 min. The absence of recording of arrhythmias and of heart rates greater than 200 beats/min (control: 400–480 beats/min) in at least two animals indicates a significant protection.

EXAMPLE J

Pharmaceutical Composition:Tablets

Tablets containing 5 mg doses of O-[(7-methoxynaphth-1-yl)methyl]-N-butyrylhydroxylamine. Formulation for preparing 1000 tablets.

| | |
|---|---|
| O-[(7-Methoxynaphth-1-yl)methyl]-N-butyrylhydroxylamine | 5 g |
| Wheat starch | 15 g |
| Corn starch | 15 g |

| | |
|---|---|
| Magnesium stearate | 2 g |
| Silica | 1 g |
| Hydroxypropyl cellulose | 2 g |

We claim:

1. A compound selected from those of formula (I):

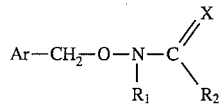

in which:

X represents oxygen or sulfur, $R_1$ represents hydrogen or a radical chosen from alkyl, cycloalkyl, cycloalkylalkyl, aryl, and arylalkyl, $R_2$ represents:
  a radical $R_{21}$ which is hydrogen or a radical chosen from:
    unsubstituted or substituted alkyl,
    unsubstituted or substituted alkenyl,
    unsubstituted or substituted alkynyl,
    and unsubstituted or substituted cycloalkyl or cycloalkylalkyl,
  or a radical $R_{22}$ chosen from:
    alkylamino in which alkyl may be unsubstituted or substituted,
    and cycloalkylamino or cycloalkylalkylamino in which cycloalkyl or cycloalkylalkyl may be unsubstituted or substituted, Ar represents an unsubstituted or substituted group chosen from:
  naphthyl,
  indolyl,
  benzofuranyl,
  benzothiophenyl,
  it being possible for Ar to be partially or totally hydrogenated, it being understood that in the description of formula (I):
the terms "alkyl" and "alkoxy" designate linear or branched groups containing 1 to 6 carbon atoms, inclusive,
the terms "alkenyl" and "alkynyl" designate unsaturated linear or branched groups containing 2 to 6 carbon atoms, inclusive,
the term "cycloalkyl" designates a group containing 3 to 8 carbon atoms, inclusive,
the term "substituted" associated with the alkyl, cycloalkyl, alkenyl, alkynyl and cycloalkylalkyl groups means that the substitution may be made by one or more radicals chosen from halogen, alkyl, and alkoxy,
the term "substituted" associated with the Ar group means that Ar is substituted with one or more radicals R, which are identical or different, chosen from halogen, hydroxyl, Ra, —$CH_2$—Ra, —O—Ra, —CO—Ra, and —O—CO—Ra (with Ra chosen from alkyl, substituted alkyl, alkenyl, alkynyl, cycloalkyl, substituted cycloalkyl, cycloalkylalkyl, substituted cycloalkylalkyl, aryl, substituted aryl, arylalkyl, and substituted arylalkyl),
and the term "substituted" associated with the expressions "aryl" and "arylalkyl" means that the substitution consists of one or more radicals chosen from halogen, alkyl, alkoxy, hydroxy, and alkyl substituted with one or more halogens;

and its enantiomers or diastereoisomer thereof.

2. A compound selected from those as claimed in claim 1, in which the Ar group is mono- or disubstituted according to one of the following formulae:

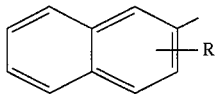 (A)

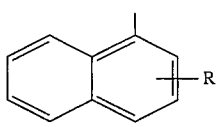 (B)

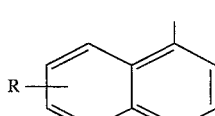 (C)

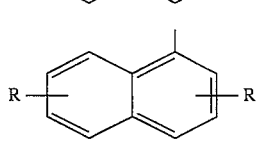 (D)

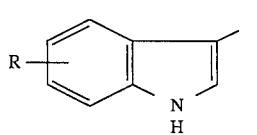 (E)

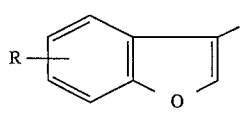 (F)

and

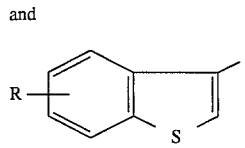 (G)

with R as defined in claim 1.

3. A compound selected from those as claimed in claim 1, in which the Ar group is mono- or disubstituted according to one of the following formulae:

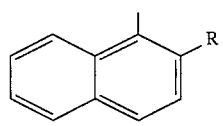 (A')

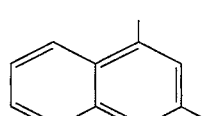 (B')

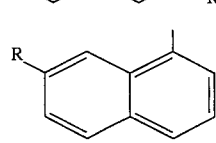 (C')

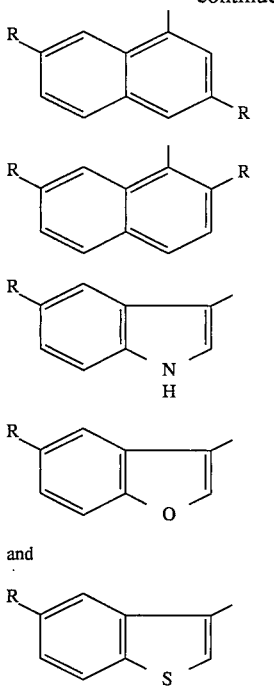

with R as defined in formula (I).

4. A compound as claimed in claim 1, which is O-[(7-methoxynaphth-1-yl)methyl]-N-acetylhydroxylamine.

5. A compound as claimed in claim 1, which is O-[(7-methoxynaphth-1-yl)methyl]-N-butyrylhydroxylamine.

6. A compound as claimed in claim 1, which is O-[(7-methoxynaphth-1-yl)methyl]-N-cyclopropylcarbonylhydroxylamine.

7. A compound as claimed in claim 1, which is O-[(2-methoxynaphth-1-yl)methyl]-N-acetylhydroxylamine.

8. A pharmaceutical composition containing at least one compound claim 1, in combination with one or more pharmaceutically-acceptable excipients.

9. A method of treating a mammal afflicted with a disorder of the melatoninergic system comprising the step of administering to the said mammal an amount of a compound of claim 1 which is effective in order to alleviate the said disorder.

10. A method of treating a mammal according to claim 9 wherein the disorder is a sleep disorder.

* * * * *

UNITED STATES PATENT AND TRADEMARK OFFICE
CERTIFICATE OF CORRECTION

PATENT NO. : 5,612,368
DATED : March 18, 1997
INVENTOR(S) : Jean Andrieux et al page 1 of 2

It is certified that error appears in the above-indentified patent and that said Letters Patent is hereby corrected as shown below:

Column 1, line 21: "6,3:" should read -- 63: --.

Column 11, line 21: Replace "Methyoxindol" with -- Methoxyindol --.

Column 15, line 54: Delete the "m" from the end of the line.

Column 15, line 55: Insert "m" before "ethyl" at the beginning of the line so as to read -- methyl --.

Column 18, line 15: Replace "Benzyl" with -- Benzoyl --.

UNITED STATES PATENT AND TRADEMARK OFFICE
CERTIFICATE OF CORRECTION

PATENT NO. : 5,612,368
DATED : March 18, 1997
INVENTOR(S) : Jean Andrieux et al

It is certified that error appears in the above-indentified patent and that said Letters Patent is hereby corrected as shown below:

Column 22, line 15:   Add a -- ) -- after "yl".

Column 22, line 16:   Remove ")" at the beginning of the line.

Column 22, line 26:   Replace "Indol-a-yl" with -- Indol-3-yl --.

Signed and Sealed this

Tenth Day of June, 1997

Attest:

BRUCE LEHMAN

Attesting Officer          Commissioner of Patents and Trademarks